United States Patent [19]

Shimoni

[11] Patent Number: 4,865,043

[45] Date of Patent: Sep. 12, 1989

[54] DECISION AND IMPLEMENTATION SYSTEM FOR MEDICAL IMAGING

[75] Inventor: Yair Shimoni, Jerusalem, Israel

[73] Assignee: Elscint, Haifa, Israel

[21] Appl. No.: 901,357

[22] Filed: Aug. 28, 1986

[30] Foreign Application Priority Data

Sep. 13, 1985 [IL] Israel ............................................ 76397

[51] Int. Cl.⁴ .................................................. A61B 5/04
[52] U.S. Cl. ..................................... 128/700; 128/702; 128/653; 128/654
[58] Field of Search ......................... 128/696, 702–705, 128/708, 653–654, 659, 661, 364, 414; 364/413.05, 413.13, 413.24

[56] References Cited

U.S. PATENT DOCUMENTS

| 4,023,564 | 5/1977 | Valiguette et al. | 128/708 X |
|---|---|---|---|
| 4,197,836 | 4/1980 | Wagner et al. | 128/659 X |
| 4,245,647 | 1/1981 | Randall | 128/659 |
| 4,458,688 | 7/1984 | VonBehren | 128/659 |
| 4,585,008 | 4/1986 | Jarkewicz | 128/659 X |
| 4,592,364 | 6/1986 | Pinto | 128/672 |
| 4,649,930 | 3/1987 | Groch et al. | 128/653 X |
| 4,694,837 | 9/1987 | Blakely et al. | 128/653 |
| 4,727,882 | 3/1988 | Schneider et al. | 128/653 |

OTHER PUBLICATIONS

Williams, R. J. et al, "A System for ECG Synchronized Gamma Com// Studies," Phys. Med. Biol. Sept. 1980 vol. 25, No. 5, pp. 935–940.

Monds, F. C. et al "Matched Filter Location of ECG Complexes", Conf. Proc. of Conf. on Applns of Elec. in Med., Southhampton Eng. 6-8 Apr. 1976.

Primary Examiner—Francis Jaworski
Attorney, Agent, or Firm—Sandler & Greenblum

[57] ABSTRACT

Data selection method and system using a plurality of multi-dimensional windows wherein two parameters of ECG signals are tested for determining whether the imaging data received simultaneously with the ECG signal is to be accepted. The plurality of windows provides a capability to gate and to sort imaging data based on the passage of associated ECG signals through each of the plurality of windows with different parameters. Thus images can be reconstructed for a populations of abnormally short or long heart cycles from a common data pool.

33 Claims, 3 Drawing Sheets

DECISION AND IMPLEMENTATION SYSTEM FOR MEDICAL IMAGING

FIELD OF THE INVENTION

This invention is concerned with physiological imaging equipment such as cardiac imaging equipment and more particularly with decision systems which decides the disposition of the imaging data in such imaging systems.

BACKGROUND OF THE INVENTION

The presently available Gamma Cameras are capable of acquiring images of the functioning of organs of the body. For example, parameters and images of heart beats are obtainable using gating methods. In general in gated methods, each heart beat is divided into a number of intervals of short time duration during which the heart imaging data is acquired. The amount of radiation collected during such an interval is much too low to provide a useable image. Therefore the acquisition is extended over a long period, for example 200–500 heart beats, and the gamma photons collected during corresponding intervals from each heart beat are added together. To be of any value only data from similar beats should be added. That is, beats in which the heart supposedly follows the same motion. Therefore a rejection mechanism is used to limit the data to beats that are sufficiently similar.

Gating is usually done based on the electro-cardiac signals, which are acquired by an electrocardiograph (ECG) amplifier. An ECG recorder enables visual inspection of this signal. The electrocardiogram (the output of the ECG recorder) is a graphical representation of the electrical signals obtained from the heart durig the acquisition of the signal. The signal's amplitude varies with time, graphically creating "shapes". As is well known the heart beat provides certain characteristics defined by amplitudes and differently shaped portions. One of the shaped portions is known in general as the R-wave and is part of the shape system known as "QRS Complex".

Gating is defined as synchronizing the images with a physiological signal. Multi-gating is defined as creating a set of images each synchronized with a different point during the cycle of the physiological signals. Different sub-methods use points defined, among other ways, on the basis of: the time from the last R-wave, the "phase" (fraction of R-R time, see below), or the time left to the next R-wave.

Rejection is discarding of data because the parameter does not fall within a proscribed window, as explained below. Rejection is one possible disposition of the data, with addition to other data is another disposition of the data. The decision as to which action to take is made by the decision systems.

Similar gated acquisition methods are used with other imaging modalities, most notably the nuclear magnetic resonance imaging (MRI or NMR). The invention is, however, not limited to the two mentioned modalities. In this description gamma cameras are used as an illustrative example only, whereas the inventive idea specifically applies to all imaging modalities using gated acquisition means and methods.

In the presently available systems the rejection mechanism is generally a temporal widow, wherein each heart beat is timed, usually by detecting the part of the electro-cardiac signal called R-wave which appears in every beat. If the beat length; i.e., R-wave to R-wave interval (R-R time for short) is outside the window then at least one beat is rejected. If a beat is too short both it and the following beat are usually rejected. This assumes both beats are not "normal". One ends abnormally and the next starts abnormally.

This rejection mechanism allows the use of the window for acquiring a series of images representing a "normal" beat, as defined by the prior art systems. The normal beat is defined by the prior art systems as a beat with an R-R time in the window where the window is usually set around the most common R-R time found during a test or learning period. Thus, the definition of "normal" is subjective as each patient has a heart beat that is normal for that person at the time of the test or learning period.

There are several drawbacks or shortcomings in the prior art systems. These drawbacks are generally caused by a one-dimensional analysis of the heart beat. Among the drawbacks in prior art systems are:

All beats within the window are accepted (not rejected) as they are considered "normal". All beats that pass through the window are not necessarily "normal" and the images are degraded by inclusion of "aberrant" beats ("normal" in R-R time but not otherwise).

There is no discrimination between different types of short (or long) beats. For example, the physiology of a certain type of short beat (premature ventricular beat or PVB) frequently causes the next beat to be longer than "normal" to compensate for the shortness. These compensatory beats should be, but are not rejected. Other types of short beats (for example premature atrial beats, or PAB) are not followed by such compensatory beats. The rejection mechanism is not optimal if it does not discriminate between the different types of short beats. The same argument holds for "long" beats.

A lot of information is lost (and consequently a lot of radiation dose to the patient is not utilized) by rejecting all "abnormal" beats.

This last shortcoming is especially serious, not only because of the "unused" or "wasted" radiation dosage but also because it results in images not truly representative of the cardiac condition. The cardiac parameters, such as cardiac output are based on the images created for a "normal" cycle. When that "normal" cycle is statistically not sufficiently representative (although it is based on the most prevalent R-R time, it may still account for less than 50% of the heart beats, say), then the parameters so obtained do not yield enough information about the patient's true cardiac condition.

This and the first two shortcomings are emphasized in the rest versus exercise comparison test, which is becoming increasingly more accepted as a procedure for cardiac examination. Many patients exhibiting essentially "normal" beats at rest start exhibiting abnormalities, such as aberrant beats or an increased prevalence of PVBs, during the stress of an exercise test.

Two other approaches are being tried today to overcome the drawbacks of presently available prior art systems. The first is sometimes referred to as "list mode" or "serial" acquisition (or several other names) and consists of listing all nuclear events, their location and timing, and later constructing the set of images for the cardiac cycle off-line. The rejection is done manually. This is a time consuming method and reduces the throughput of the clinic. At the same time it is still not optimal as it still uses only the R-R times as the basis for rejection.

The second approach consists of having several R-R windows. In some cases, where a single very specific cause creates all abnormal beats this sufficies. However, in most cases short heart beats may have widely differing electrical and mechanical shapes, determined usually by the position of the abnormal site (locus) of the "firing" mechanism and therefore this second approach does not usually overcome the drawbacks of the available systems.

It should be noted that additional information about the heart's condition does exist. This is the electrocardiogram (ECG) tracing, which follows the electrophysiological signals from the heart. These signals are determined by the route and speed of the electrical pulses which cause the heart muscles to contract and expand. These pulses, in travelling from the location of the "firing" mechanism to and through the heart muscles, radiate electromagnetic waves which are detected by the ECG's electrodes.

The pulse causing ventricular contraction is detected as part of the signal called the "QRS complex". It is distinctive and provides information about the ventricular contraction phase and about many defects in the ventricular contraction. Other parts of the signal teach about other phases, e.g. atrial contraction (P-wave), ventricular expansion (T-wave) etc. However, this other information is not usually used for gating purposes in current systems.

Therefore, it is an object of this invention to provide a system that uses ECG-based information in addition to the R-R time (e.g. the QRS shape) to obtain more data about each heart beat and to thereby base the decision about using or rejecting the acquired imaging data on more solid ground. At the same time it enables selecting more than one beat type, where again the type of heart beat is decided on the basis of both R-R time and QRS shape. The system provided herein can be also used to decide acceptance or rejection in conjunction with imaging acquisition gating some other physiological signal, e.g. a spirometric signal, measuring breathing.

DESCRIPTION OF THE INVENTION

Accordingly, a system for performing on-line or off-line decisions about rejection or acceptance of cardiac imaging data and the disposition thereof is provided.

This system reduces the amount of data which is rejected and at the same time provides image sets which follow the mechanical motion of the heart for the beat type selected more closely than existing systems.

In addition, the system enables selecting more than one beat type to be imaged from the same acquired data, either on-line or off-line.

More particularly a data acquisition method for use with medical imaging equipment is provided, said method comprises the steps of:
selecting a plurality of multi-dimensional windows defining simultaneously the ranges of acceptance for several parameters of an ECG signal acquired during the same beat,
simultaneously acquiring cardiac imaging data and the ECG signal from the same patient,
determining for each heart beat whether the acquired ECG signal passes through the said multi-dimensional windows, and
accepting the imaging data for said each heart beat responsive to the passage of the ECG signal through any of the said multi-dimensional windows, and sorting the imaging data according to which of the plurality of multi-dimensional windows passed the ECG signal.

According to a feature of the invention a two-dimensional window is used.

According to another feature of the invention the two dimensions are time duration and shape dependent parameters of the ECG signal.

A related feature of the invention provides for one dimension being a time duration dimension and the other dimension being a shape related dimension, such as the correlation with a template.

Another related feature of the invention utilizes a linear correlation coefficient when calculating the shape related parameter of the two dimensional window.

Yet another related feature of the invention utilizes ECG data acquired during a first set period to form templates for shape correlations.

According to yet another feature of the invention the imaging data is nuclear radiation (scintigraphic) data, collected e.g. by a gamma camera.

According to another feature of the invention the imaging data is data acquired from excited nuclei, during e.g. an MRI procedure.

Yet another feature of the invention uses a number of such two dimensional windows, for the same imaging data, that is a single acquisition is used from which several different sets of images are formed.

Still another feature of the invention provides for acquiring the imaging data and makes the decision on-line, to provide images substantially during the examination.

A still further feature of the invention provides for acquiring the data in "list" mode, i.e. the data is provided to a memory without on-line imaging; Imaging is accomplished at a later time.

Yet another feature of the invention provides for parallel on-line operation of the system. The parallel multi-gated acquisition in this application is defined as the use of a multiplicity of simultaneous acceptance windows instead of a single acceptance window and rejecting only beats not within any of the windows. The acceptance of the data into any one of the windows is checked in parallel.

Yet a further feature of the invention includes acquiring ECG data over a first set period prior to the said simultaneous acquisition for determining said two dimensional window.

The above mentioned and other features and objects of the present invention will be best understood when considered in the light of the following description of a broad aspect of the present invention taken in conjunction with the following drawings, in which.

GENERAL DESCRIPTION

Figure 1:
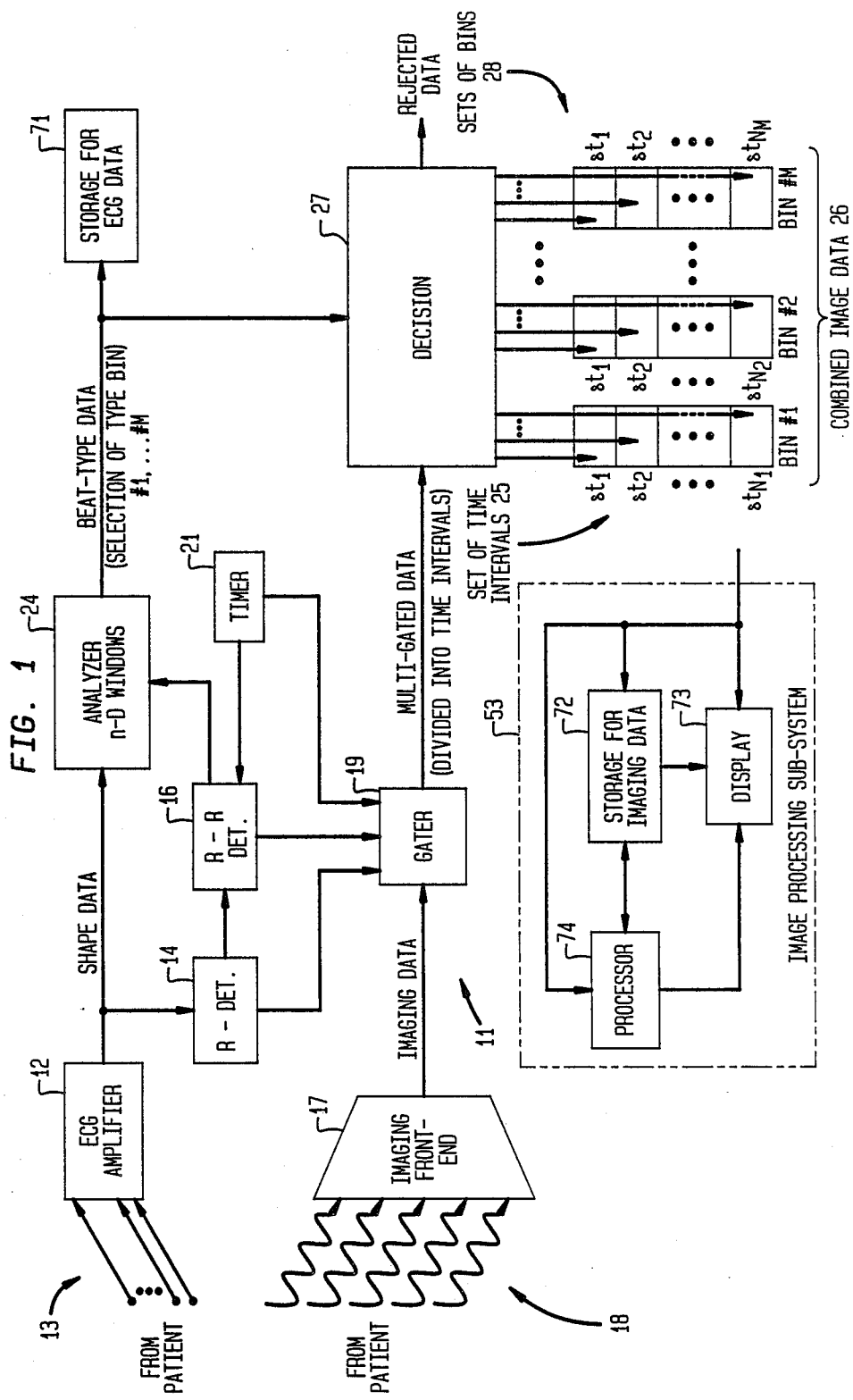
FIG. 1 is a block diagram of the inventive system generally showing on-line decision capability during simultaneous acquisition of imaging data and electrophysiological data.

A decision system for use with imaging equipment is shown generally at 11 in FIG. 1. It includes an ECG amplifier 12, which receives the electrocardiac signal data over leads 13 coming from a patient. The system of the preferred embodiment described herein detects the R-wave from the output of the ECG, using an R-wave detector 14. The interval between R-waves is measured in time units by R-R detector 16 to provide the "wavelength" of the R-wave or the distance between consecutive R-waves. The basic time for detector 16 is provided by timer (clock) 21.

The ECG equipment is used herein, among other things, for gating an imaging means, shown as the imaging front end 17. This may be a standard gamma camera well known to those skilled in the art, initially invented by Dr. H. Anger and described in U.S. Pat. No. 3,011,057, or any other imaging device used for cardiac examinations. The imaging front end receives radiation shown generally at 18 from the patient and converts that radiation into electrical signals.

In order to get either a stop motion type of image or a set of images that enables a motion-picture-like (Cine) display of the heart the output of the imaging front end is gated using gate 19 provide synchronization with the heart. The gate 19 is operated responsive to timer 21, the detected R-wave from unit 14 and the R-R time as determined by unit 16 to transmit imaging data divided into time intervals. The gated imaging data is thus sub-divided into intervals and is synchronized with the R-wave.

The R-R time and the ECG curve shape or the shape of the QRS portion of the ECG curve are analyzed in analyzer 24 to provide multi-dimensional windows. Ideally, a window is provided for every type of heart beat. The ECG data together with the R-R times and at the user's discretion the types of heart beats as analyzed by analyzer 24 are stored in storage unit 71 for further use. The output of the analyzer 24 includes tags on the ECG data in accordance with the multi-dimensional windows through which the ECG data passed. Thus the ECG data becomes heart-beat type data after analysis by analyzer 24.

The heart beat type data is transmitted to decision circuit 27. The decision circuit sorts the imaging data of the heart beat in question, arriving from gate 19, by transmitting it to selected ones of the bins in the set of bins 28 if the beat type passes through one of the windows. Otherwise the data is rejected. Thus the decision circuit is a filter or sorting type circuit that sorts the imaging data, heart beat by heart beat, using the tags in the analyzer output.

Each bin in the set of bins 28 corresponds to a distinct window in analyzer 24 and comprises a number of divisions, corresponding to the intervals into which the appropriate heart beat has been sub-divided for multi-gating by the gater as indicated at 25. The number of intervals used for different beat types may be different. For example if the intervals are fixed time intervals than beats of different lengths will comprise a different number of intervals. The data from all heart beats which are similar in type and pass through the same window are accumulated in the same bin.

The image data which is generally combined at 26 is further transmitted to storage 72 and/or to display 73. The data may also be processed in processor 74. In short, the data is then transmitted to the image processing sub-system 53 of the imaging equipment.

In a slightly different version: the gate 19 only synchronizes the imaging data with the ECG data (R-wave), but the data of the heart beat is kept in list-mode-like version (a list of data amplitude and location versus time) until it is sub-divided into appropriate intervals by the decision unit 27, according to the beat type and the bin number.

Figure 2:
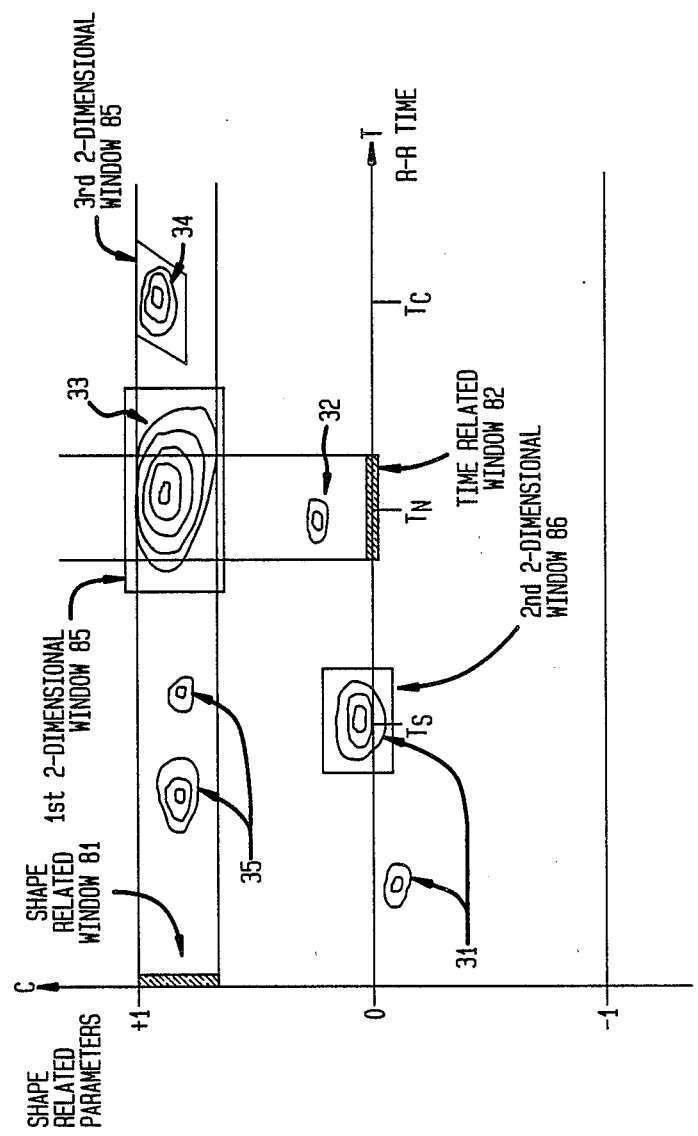
FIG. 2 is a graphical representation of the acquired data analyzed in accordance with the present invention as a function of two dimensions.

FIG. 2 shows data that falls within a set criteria having two dimensional parameters for example. The parameters shown in FIG. 2 are shape and time related, for example the correlation, along the ordinate and the time between consecutive R-waves (R-R time) along the abscissa. Preferrably the whole possible two dimensional range of the parameters is divided into windows and thereby each heart beat is tagged or typed. The number of different sets of two dimensional parameters (two-dimensional windows) that can be used, however, is limited by the memory of the system. Generally, three or four windows are enough to provide excellent images while efficiently utilizing data that has conventionally been discarded.

FIG. 2 shows iso-density lines displaying statistics for exemplary data. If each heart beat is denoted as a dot in the two-dimensional space of FIG. 2, these lines connect points with equal dot-density. Therefore, if a first line is surrounded by a second line, the first line (the inner one) denotes higher density and therefore a higher frequency of occurence of heart beats whose R-R time and correlation lie within the region circumscribed by said first line.

In the example several regions of high density are shown. The one with highest density (most prevalent) is number 33, defining the "normal" R-R time Tn and shape.

A one-dimensional window 82 is shown, using only the R-R time. It is shown that this window includes both the "normal" beats region 33 and a high density region 32 of "aberrant" beats, having the "normal" R-R time but not the "normal" shape.

It is also shown that a window set around Ts, the R-R time of a short beat, may include two differently shaped groups, a PVB region 31 and a PAB region 35.

A one-dimensional window 81 using only the shape of the ECG signal part called the QRS Complex may also include several beat types. These all have the "normal" shape but widely differing lengths, and include the "normal" beats 33, the PABs 35 and the "compensatory" beats 34, having a R-R time Tc=2Tn-Ts (so that Ts+Tc=2Tn, compensating for Ts).

FIG. 2 shows how the use of a two-dimensional window 85 clearly distinguishes the "normal" beats from all other types. Similarly, the two-dimensional window 86 clearly distinguishes one type of PVBs from all other beat types.

FIG. 2 shows that the windows do not have to be specified independently for R-R time and for correlation (thereby yielding a rectangular window in those coordinates). On the contrary, a more complex window such as two-dimensional window 87 can be defined for better distinguishability between beat types.

By utilizing both parameters the data is reliably separated and two-dimensional (or multi-dimensional) windows can be used to gate incoming acquired imaging data.

Figure 3:
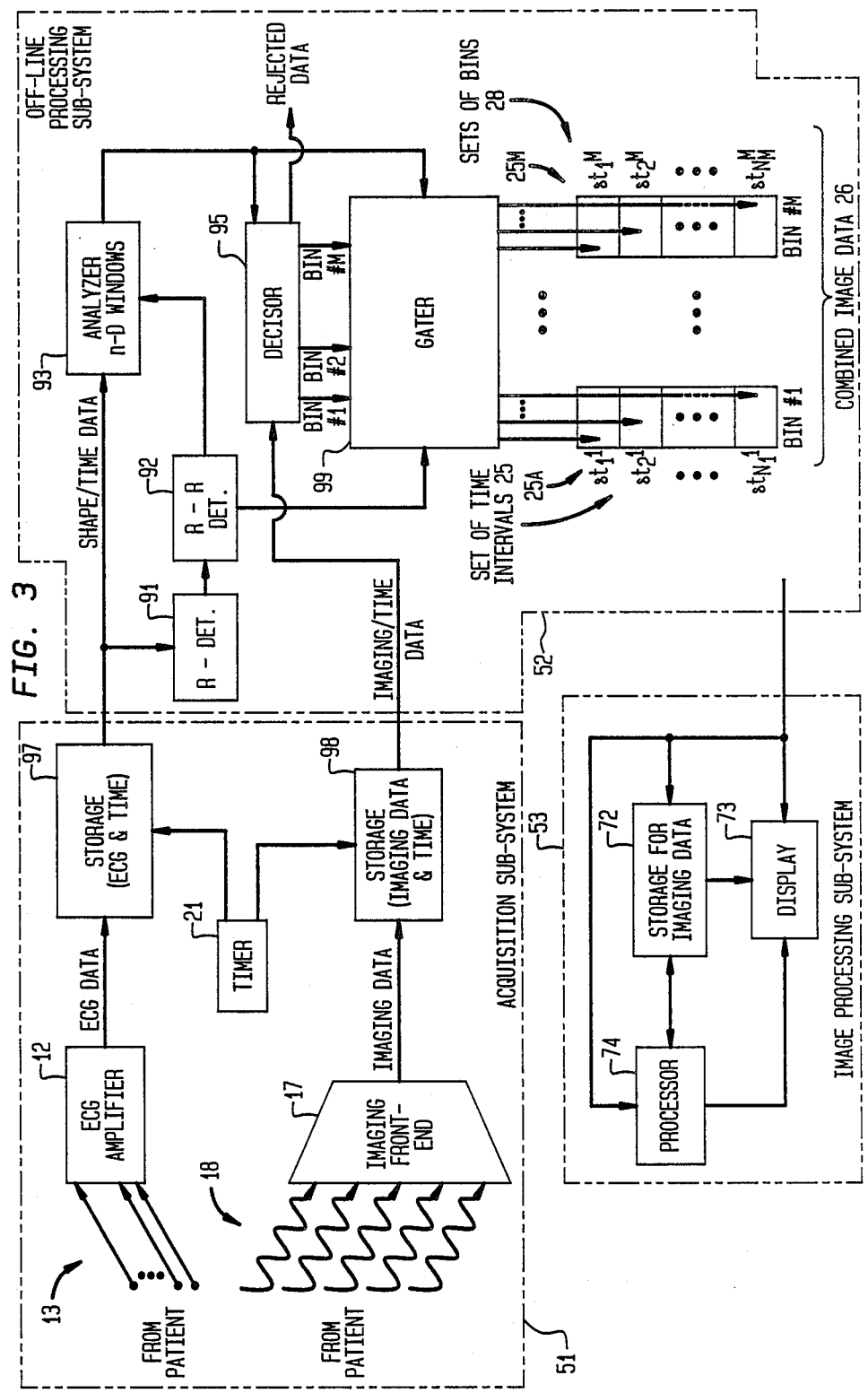
FIG. 3 is a block diagram of an inventive system generally showing off-line decision capability after simultaneous acquisition of imaging data and electrophysiological data.

The decision system for off-line use with imaging systems is shown in FIG. 3 generally as aquisition, off-line processing and image processing subsystems 51,52 and 55, respectively. The acquisition subsystem 51 includes an ECG amplifier 12, which receives the electrocardiac signal data over leads shown generally at 13 coming from the patient. (In general, the some parts in FIGS. 1 and 3 bear the same numbers) The system of the preferred embodiment described herein stores the ECG data and the timing data from timer 21 in storage 97. In a slightly different version an R-detector may be applied at this stage and the R-wave occurrence times may also be stored in storage 97.

Since the ECG equipment is used herein among other things for gating an imaging means the imaging front end is shown at 17. The imaging front end receives radiation shown generally at 18 from the patient and converts that radiation into electrical signals. The imaging data together with timing data from time 21 are stored in storage 98.

At some time, after the end of acquisition, the ECG data is read by off-line processing subsystem 52 from storage 97 and analyzed in analyzer 93. For the purpose of this analysis the ECG data is also transferred to an R-wave detector 91 and an R-R time determiner 92 and the R-R times are also input to analyzer 93. R-wave detector 91, R-R time determiner and analyzer 93 may be different from their counterparts 14, 16 and 24 in FIG. 1 in that they operate off-line and therefore may be slower and at the same time more sophisticated.

Also after acquisition, the imaging data is read by off-line processing subsystem 52 from storage 98 into decision unit 95. This unit, working off-line, bases its decision as to the disposition of the imaging data on the beat type information it obtains from analyzer 93. Working off-line it is possible to reach more sophisticated decisions then is possible when working on-line. For example, it is possible to use overlapping windows, as two copies of the data can be sent to two different bins. While overlapping windows are possible in principle in on-line decision making, it usually takes too much computer time and effort and is not contemplated in the near future.

The imaging data is relegated by the decision unit to different bins or is rejected, based on which window the corresponding ECG data matched. The data which is allocated to a bin then passes to a multi-gater 99, which sub divides it into the appropriate time intervals.

Again, working off-line, it is much easier to use not only a different number of intervals for different bins (beat types) but also to have each interval different in duration and specific to its bin and its ordinal number within the bin. Thus the data is sent to bins 1-m in set 28, each having its individual set of time intervals 25a to 25m.

It should be noted that working off-line, the off-line processing system 52 may read the same data stored in ECG storage 97 and in imaging data storage 98 several times, each time having the analyzer 93 make different analyses, based on different templates. Similarly, the decision unit 95 may make different decisions each time as to which data types it accepts and which it rejects. Again similarly, the gating unit or gate 99 may make different sub divisions, into different time intervals, of the same beat type at different readings.

The data from all heart beats which are similar in type and pass through the same window are accumulated in the same bin. The image data which is generally combined as 26 is further transmitted to image processing subsystem 53, comprising a processor 74 for image and other processing, storage 72 and display means 73.

Thus a system is provided for using several parameters of ECG data to classify all or almost all of the heart beats of the patient during a test. The multi-gated imaging data is sorted into bins according to the classifications. Subsequently the data of certain classes may be rejected. However, the rest of the data is used to provide the images. The system may operate on-line or off-line but in either case uses data that previously was erroneously rejected and wasted.

While the invention has been described in respect to certain specific examples it should be understood that these embodiments are examplary only and are not limitations on the invention which is defined by the following claims.

What is claimed is:

1. A decision making and implementing method for use with a diagnostic medical imaging system for examining a patient, said method comprising the steps of:
   using a plurality of multi-dimensional windows to examine parameters of an electrocardiograph (ECG) signal received from said patient,
   simultaneously acquiring imaging data and said ECG signal from the same patient,
   determining whether the acquired ECG signal passes through any of said plurality of multi-dimensional windows,
   accepting the imaging data responsive to the passage of the simultaneously acquired ECG signals through any of said plurality of multi-dimensional windows, and
   sorting the accepted imaging data according to said any of said plurality of multi-dimensional windows through which the simultaneously acquired ECG signal passed.

2. The method of claim 1 wherein said parameters comprise R to R time of the ECG signal.

3. The method of claim 1 including the step of displaying the imaging data.

4. The method of claim 1 including a step of storing the data before said step of determining whether the said ECG signal passes through any of said plurality of multi-dimensional windows.

5. The method of claim 4 wherein said storing is done in time sequence mode.

6. The method of claim 1 including simultaneously supplying each of said plurality of multi-dimensional windows with said ECG signal.

7. The method of claim 6 including the step of acquiring said ECG signal over a first set period prior to the step of simultaneously acquiring imaging data and the ECG signal, and
   determining said multi-dimensional window from the prior acquired signal.

8. The method of claim 7 wherein said parameters are the time duration between consecutive R waves in the simultaneously acquired ECG signal and the amplitude versus time shape of the simultaneously acquired ECG signal.

9. The method of claim 7 wherein said determining step includes the step of comparing the amplitude versus time shape of the ECG signal and a template.

10. The method of claim 9 wherein said comparing step includes finding a correlation coefficient.

11. The method of claim 10 wherein said correlation coefficient is a linear correlation coefficient.

12. The method of claim 1 wherein said at least some of said plurality of windows are overlapping windows.

13. The method of claim 1 including the step of dividing the binned imaging data into sub-divisions in accordance with time intervals between the multi-dimensional windows.

14. The method of claim 1 wherein said plurality of windows include windows formed with different templates.

15. The method of claim 1 wherein said step of storing includes summing in the same bin data from different intervals between consecutive R waves having the same classification.

16. The method of claim 1 wherein said imaging data is nuclear imaging data.

17. A decision making and implementing system for use with medical diagnostic imaging equipment used for examining a patient, said system comprising:
  means for simultaneously acquiring imaging data and an ECG signal from the same patient,
  analyzer means for determining whether the acquired ECG signal passes through any of a plurality of multi-dimensional windows,
  gating means for accepting the imaging data responsive to the passage of the simultaneously acquired ECG signal through said any of said plurality of multi-dimensional windows, and
  sorting means for sorting said accepted imaging data according to the any of said plurality of multi-dimensional windows through which the simultaneously acquired ECG signal passed.

18. The system of claim 18 wherein said parameters comprise amplitude versus time shape of the ECG signal.

19. The system of claim 17 wherein said parameters comprise the R-R time of the ECG signal.

20. The system of claim 17 including means for displaying the imaging data.

21. The system of claim 20 including means for storing the data before operating said analyzer means.

22. The system of claim 21 wherein said means for storing comprises means for storing in a time sequence.

23. The system of claim 17 wherein said analyzer means comprises means for on-line determining operated during acquisition.

24. The system of claim 1 including means for simultaneously supplying said plurality of multi-dimensional windows with said ECG signal.

25. The system of claim 17 including the means for acquiring said ECG signal over a first set period prior to simultaneously acquiring imaging data and the ECG signal, and
  means for determining said multi-dimensional window from the prior acquired signal.

26. The system of claim 25 including means for comparing the shape of the ECG signal and a template to determine said similarity.

27. The system of claim 26 wherein said means for comparing includes means for finding a correlation coefficient.

28. The system of claim 27 wherein said correlation coefficient is a linear correlation coefficient.

29. The system of claim 17 wherein at least some of said plurality of windows are overlapping windows.

30. The system of claim 17 including means for storing the accepted imaging data in bins according to the sorting.

31. The system of claim 30 wherein said means for storing includes means for summing in the same bin data from different intervals between consecutive R waves having the same classification.

32. The system of claim 17 wherein said imaging data is scintigraphic imaging data.

33. The system of claim 17 wherein said imaging data is magnetic resonance imaging data.

* * * * *